(12) United States Patent
Amano

(10) Patent No.: US 7,815,657 B2
(45) Date of Patent: Oct. 19, 2010

(54) CORNEAL SURGICAL APPARATUS

(75) Inventor: Masanori Amano, Aichi (JP)

(73) Assignee: Nidek Co., Ltd., Aichi (JP)

( * ) Notice: Subject to any disclaimer, the term of this patent is extended or adjusted under 35 U.S.C. 154(b) by 514 days.

(21) Appl. No.: 11/488,598

(22) Filed: Jul. 19, 2006

(65) Prior Publication Data

US 2007/0027462 A1 Feb. 1, 2007

(30) Foreign Application Priority Data

Jul. 20, 2005 (JP) ............................ P2005-210641
Jul. 20, 2005 (JP) ............................ P2005-210642

(51) Int. Cl.
*A61F 9/00* (2006.01)
(52) U.S. Cl. .................................... 606/166
(58) Field of Classification Search ................ 606/166, 606/167, 180, 107, 108, 161, 172; 30/123.5; 600/562, 564, 565, 570, 571; 623/4.1–6.12
See application file for complete search history.

(56) References Cited

U.S. PATENT DOCUMENTS

| | | | |
|---|---|---|---|
| RE35,421 E | 1/1997 | Ruiz et al. | |
| 5,624,456 A | 4/1997 | Hellenkamp | |
| 5,976,163 A | 11/1999 | Nigam | |
| 5,980,543 A * | 11/1999 | Carriazo et al. | ............. 606/166 |
| 2003/0018348 A1 | 1/2003 | Pallikaris et al. | |
| 2003/0130676 A1 | 7/2003 | Sugimura et al. | |
| 2004/0260320 A1 | 12/2004 | Lisk, Jr. et al. | |
| 2004/0260321 A1 | 12/2004 | Tai et al. | |
| 2005/0197620 A1 * | 9/2005 | Tu | ............................... 604/26 |
| 2005/0288696 A1 * | 12/2005 | Pallikaris et al. | ............. 606/166 |

FOREIGN PATENT DOCUMENTS

JP 2003-175071 6/2003

* cited by examiner

*Primary Examiner*—Anhtuan T Nguyen
*Assistant Examiner*—Ashley Cronin
(74) *Attorney, Agent, or Firm*—Finnegan, Henderson, Farabow, Garrett & Dunner, L.L.P.

(57) ABSTRACT

A corneal surgical apparatus for incising a cornea in a flap shape, includes: a body portion; and a cutting head unit that is movable back and forth with respect to the body portion and includes a blade holder for holding a blade oscillationally. The cutting head unit includes a cornea applanater mounted through an applanater support for applanating the cornea substantially flatly, the cornea applanater moving forward as the cutting head unit moves forward, and the applanater support includes a movable portion for moving the cornea applanater in a direction apart from the blade holder.

2 Claims, 9 Drawing Sheets

CORNEAL SURGICAL APPARATUS

BACKGROUND OF THE INVENTION

The present invention relates to a corneal surgical apparatus for incising a cornea in a flap shape.

As corneal refractive surgery, there has been widely adopted the LASIK (laser assisted in situ keratomileusis) method, in which a flap is formed by incising a portion ranging from a corneal epithelium to a corneal stroma, the corneal stroma is ablated by opening the flap and irradiating it with a laser beam, and the flap is returned (closed) to the initial state. In recent years, however, there has been proposed a new method called the Epi-LASIK (Epithelial LASIK), in which a flap (as will be called a "corneal epithelium flap") is formed by incising and peeling only a portion of the corneal epithelium and then the corneal stroma is ablated by irradiating it with the laser beam. The corneal surgical apparatus for the Epi-LASIK for preparing the corneal epithelium flap is also proposed. In this apparatus, the corneal epithelium flap is prepared by moving (forward) a blade, which is being oscillated at a high speed in an edge width direction of the blade, in a peeling (incising) direction of the corneal epithelium to a predetermined position. After the corneal epithelium flap is prepared, the blade is moved (backward) in the direction backward of the peeling direction to the initial position.

In the aforementioned apparatus for the Epi-LASIK, some is equipped with a cornea applanater for applanating the cornea substantially flatly prior to the blade to be moved forward, but another is not. The former is advantageous in that it can peel the corneal epithelium uniformly, but has a problem that the corneal epithelium flap may be broken or extended by the friction with the cornea applanater when the blade is moved backward to the initial position after the flap was prepared. On the other hand, the latter does not have the same problem, but has another problem that the corneal epithelium may not be uniformly peeled off.

SUMMARY OF THE INVENTION

In view of the problems, therefore, the invention has an object to provide a corneal surgical apparatus which can incise a cornea satisfactorily into a flap shape and which can prepare a satisfactory corneal epithelium flap.

In order to solve the problems, the invention is characterized by the following arrangements.

(1) A corneal surgical apparatus for incising a cornea in a flap shape, comprising:
 a body portion; and
 a cutting head unit that is movable back and forth with respect to the body portion and includes a blade holder for holding a blade oscillationally,
 wherein the cutting head unit includes a cornea applanater mounted through an applanater support for applanating the cornea substantially flatly, the cornea applanater moving forward as the cutting head unit moves forward, and
 wherein the applanater support includes a movable portion for moving the cornea applanater in a direction apart from the blade holder.

(2) The corneal surgical apparatus according to (1), wherein, with the movable portion, the cornea applanater is always kept at a predetermined distance from the blade holder when the cutting head unit moves forward and is gradually moved away from the blade holder when the cutting head moves backward.

(3) The corneal surgical apparatus according to (1), wherein at least one of the applanater support and the cutting head unit includes a limit portion for restricting the movement of the cornea applanater toward the blade holder.

(4) The corneal surgical apparatus according to (1), wherein the applanater support includes a finger hook to be hooked by a finger of an operator gripping the body portion so that the cornea applanater is moved in the direction apart from the blade holder by the movable portion when the finger hook is pulled.

(5) The corneal surgical apparatus according to (1), further comprising:
 a suction ring adapted to be sucked and fixed on a patient's eye; and
 a retaining portion that is disposed on one of the body portion and the suction ring and extends in the forward direction of the cutting head unit,
 wherein the applanater support includes an abutment portion which abuts against the retaining portion when the cutting head unit moves forward to a predetermined position, so that the cornea applanater is moved in the direction apart from the blade holder by the movable portion when the cutting head unit further moves forward from the predetermined position.

(6) The corneal surgical apparatus according to (1) further comprising:
 a suction ring adapted to be sucked and fixed on a patient's eye; and
 a guide portion that is disposed on one of the body portion and the suction ring and extends in the forward direction of the cutting head unit,
 wherein the applanater support includes an engagement portion to be engaged with the guide portion, and
 wherein the cornea applanater is moved in the direction apart from the blade holder by the movable portion when the cutting head unit moves forward and the engagement portion is guided to a predetermined position by the guide portion.

DETAILED DESCRIPTION OF PREFERRED EMBODIMENTS

Figure 1:
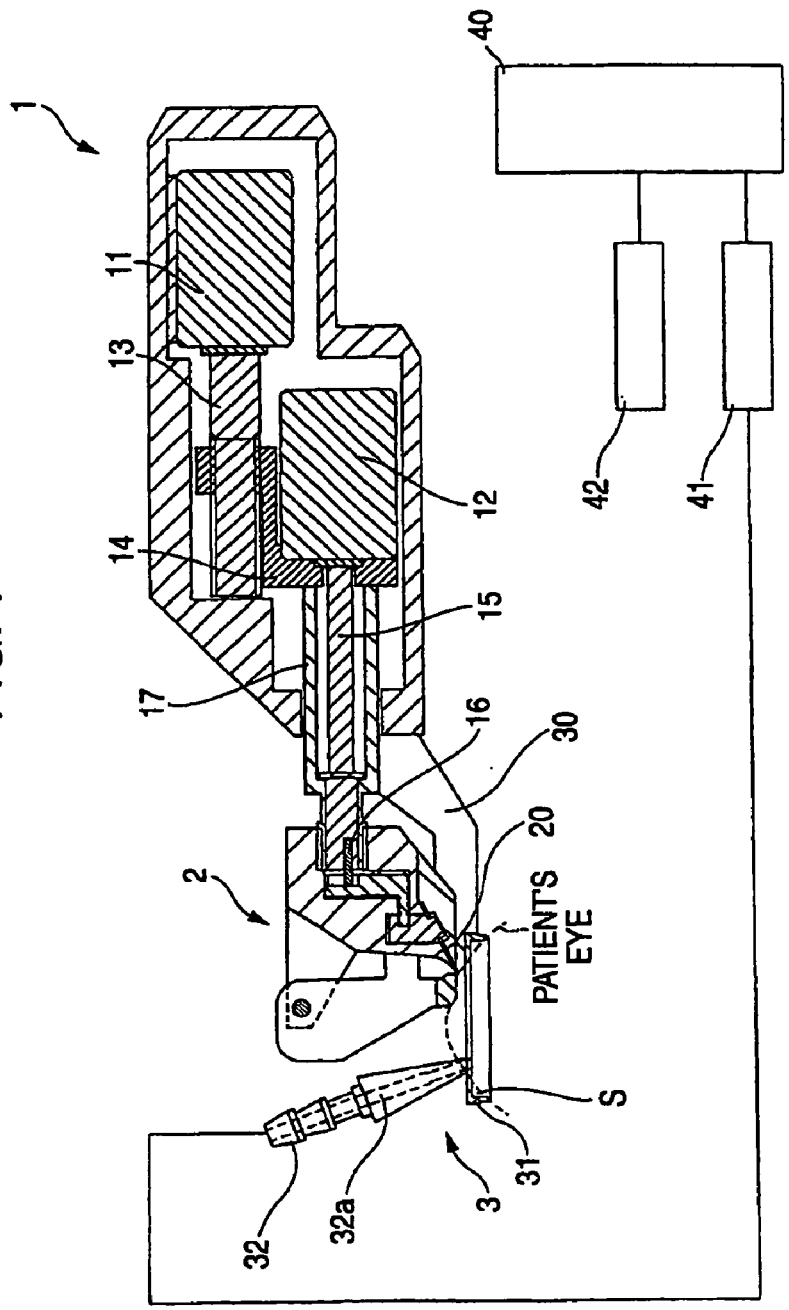
FIG. 1 is a schematic configuration diagram of a corneal surgical apparatus according to the invention.

Embodiments of the invention will be described with reference to the accompanying drawings. FIG. 1 is a schematic configuration diagram of a corneal surgical apparatus according to the invention.

First Embodiment

The corneal surgical apparatus is provided, on the front side (on the lefthand side of FIG. 1) of a body portion (a hand piece portion) 1, with: a cutting head unit 2 which is a blade holder unit that detachably and oscillationally holds a blade 20 for incising and peeling a cornea; and a suction ring unit 3 for fixing the body portion 1 on the patient's eye (an eye to be operated). The suction unit 3 is sucked and fixed to the portion of the patient's eye from the corneal limbus to the conjunctiva.

The body portion 1 houses a translation motor 11 for rectilinearly moving (translating) the cutting unit 2 over the suction unit 3 in a direction of peeling (incising) the corneal epithelium, and an oscillation motor 12 for oscillating the blade 20 at a high speed in an edge width direction of the blade 20. A connecting member 14 is threaded to a feed screw 13 fixed on a rotating shaft of the motor 11, and the motor 12 and a connecting member 17 are fixed to the connecting member 14. As the motor 11 rotates forward and backward, the motor 12 and the connecting member 17 are rectilinearly moved back and forth through the screw 13 and the connecting member 14 so that the cutting unit 2 is also rectilinearly moved back and forth. A rotating shaft 15 fixed to the rotating shaft of the motor 12 is rotatably held by the connecting member 17. An eccentric pin 16 is embedded in the distal end of the shaft 15 at a position eccentric from the center of rotation.

Figure 2:
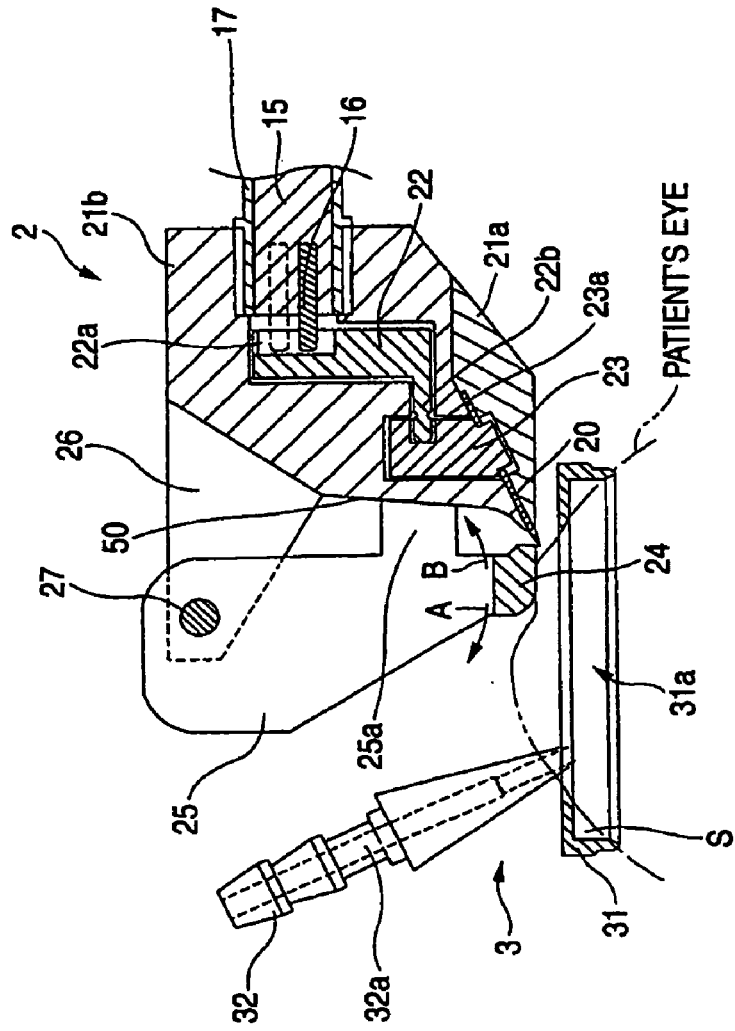
FIG. 2 is an enlarged diagram of FIG. 1 on a cutting head unit and a suction ring unit.

FIG. 2 is an enlarged view of FIG. 1 and shows the cutting unit 2 and the suction unit 3. The cutting unit 2 includes blade holders 21a and 21b for holding the blade 20 oscillationally, and a first oscillation transmission member 22 and a second oscillation transmission member 23 for converting the circumferential motions of the pin 16 by the rotations of the shaft 15 into oscillations and transmitting the motions to the blade 20. The holder 21b has a hole, into which the shaft 15 is inserted, to fix the leading end portion of the connecting member 17.

Figure 3:
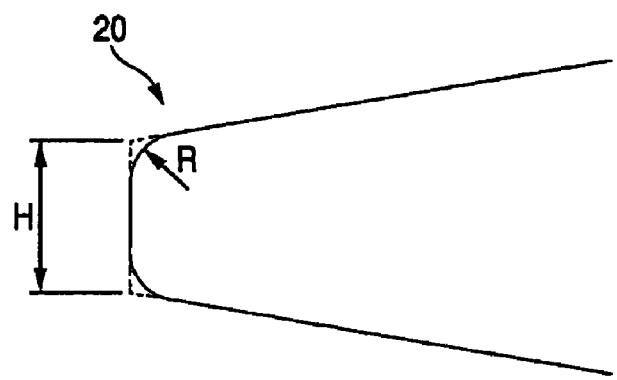
FIG. 3 is a diagram for explaining the shape of the edge of a blade.

As the blade 20, a metallic blade using stainless, steel or the like as its edge, a mineral blade using a diamond, sapphire or the like as its edge, a resin blade, and a ceramic blade are employed. The blade 20 is oscillationally held between the holder 21a and the holder 21b at an angle of 25 degrees with respect to a horizontal plane. The blade 20 is shaped, as shown in FIG. 3, to have an edge height H of 1 to 50 microns and a corner radius R of 0.5 to 25 microns (as referred to US2003/0130676A1 (JP-A-2003-175071).

In the holder 21a, a shallow recess is formed in the portion where the blade 20 is placed, and the recess has a width larger than the oscillating width of the blade 20. The holder 21a is detachably fixed on the holder 21b by not-shown screws.

The first transmission member 22 is oscillationally held in a receiving groove formed in the holder 21b. A longitudinal groove 22a engaged with the pin 16 is formed in the first transmission member 22. As the shaft 15 is rotated by the rotational drive of the motor 12, a moving force in the direction perpendicular (as will be called the transverse (lateral) direction) to the rotating axis of the shaft 15 is applied to the first transmission member 22 by circumferential motion of the pin 16 engaged with the longitudinal groove 22a. As a result, the first transmission member 22 oscillates in the transverse direction.

The second transmission member 23 is oscillationally held in a receiving groove which is formed by the holders 21a and 21b. A protrusion 22b is formed in the lower portion of the first transmission member 22, and a longitudinal groove 23a to be engaged with the protrusion 22b is formed in the second transmission member 23. When the first transmission member 22 is transversely oscillated by the rotation of the shaft 15 (or by the circumferential motion of the pin 16), a further transverse moving force is applied to the second transmission member 23 by the oscillation of the protrusion 22b engaged with the longitudinal groove 23a. As a result, the second transmission member 23 is transversely oscillated, and the blade 20 fixed to the second transmission member 23 is transversely oscillated.

A cornea applanater 24 is disposed on the front side (on the lefthand side of FIG. 2) of the cutting unit 2 (the blade 20), and applanates the cornea substantially flatly prior to the blade 20. An applanater support 25 for supporting the applanater 24 is so supported by a connecting member 26 as can rotate about a pivot pin 27 extending perpendicular to the peeling direction or the rotating axis of the shaft 15. The connecting member 26 is connected to the holder 21b. The applanater support 25 is constituted to have a center of gravity on the front side of the pin 27 (a weight may be attached), and to support the applanater 24 such that the applanater 24 is positioned closer to the cutting unit 2 (the blade 20) than the pin 27 so that a backward rotating force (in a direction B) tends to be applied to the applanater 24. When a protrusion 25a formed at the applanater support 25 on the side of the holder 21b abuts against a flat face 50 of the holder 21b on the side of the applanater support 25, the rotation of the applanater support 25 toward the cutting unit 2 (the blade 20) is restricted to keep the applanater 24 and the cutting unit 2 (or the blade 20) at a predetermined distance. It is sufficient that this limit mechanism for restricting the rotation of the applanater support 25 in the direction toward the cutting unit 2 (the blade 20) is disposed on at least one of the applanater support 25 and the cutting unit 2 (or the holder 21b). For example, the protrusion may be formed on the holder 21b while the applanater 24 being left flat.

In order to peel (separate) the corneal epithelium from the Bowman's membrane, the edge tip of the blade 20 relative to the lower face of the applanater 24 is positioned lower by the thickness of the corneal epithelium. Moreover, the spacing between the lower face of the applanater 24 and the edge tip of the blade 20 is preferred to be 300 microns or less.

The suction unit 3 includes a suction ring 31 and a suction pipe 32. The ring 31 of a generally cylindrical shape to be brought into abutment against the patient's eye is fixed to the body portion 1 by a fixing member 30, and has an opening 31a. When the ring 31 is arranged on the patient's eye, the cornea protrudes from the opening 31a, so that the lower end of the ring 31 and the open end of the opening 31a abut against the patient's eye thereby to retain a suction space S. The pipe 32 is fixed to the ring 31 and is connected to a pump 41 through a not-shown tube. When air in the space S is sucked through a suction passage 32a in the pipe 32 by the drive of the pump 41, the ring 31 is sucked and fixed on the patient's eye.

An operation of the apparatus having the above-described arrangement will be described. At first, the ring 31 is arranged on the patient's eye. Then, the pump 41 is activated to suck air in the space between the ring 31 and the patient's eye, thereby to suck and fix the ring 31 on the patient's eye. Next, a foot switch 42 is operated to cause a control unit 40 to rotationally drive the motor 12 and the motor 11.

The blade 20 is transversely oscillated by the rotational drive of the motor 12 and is moved forward in the direction of peeling the corneal epithelium together with the cutting unit 2. With these oscillations and forward movements of the blade 20 and with the shape of the blade edge, the corneal epithelium is incised and peeled from the underlying Bowman's membrane so that the corneal epithelium flap is prepared.

The applanater 24 is so supported rotatably in the peeling direction through the applanater support 25 and the connecting member 26 as to applanate the cornea substantially flatly prior to the blade 20. As the cutting unit 2 moves forward, the backward rotating force (in the direction B) around the pin 27 is applied to the applanater 24 by the reaction from the cornea and the frictional force with the cornea. The backward rotation of the applanater support 25 is, however, restricted by the protrusion 25a of the applanater support 25 and the face 50 of the holder 21b to always keep the distance constant between the applanater 24 and the cutting unit 2 (the blade 20). As a result, the cornea is applanated by the cornea applanater 24 so that the corneal epithelium flap of a uniform thickness can be prepared irrespective of the corneal shape.

Figure 4A:
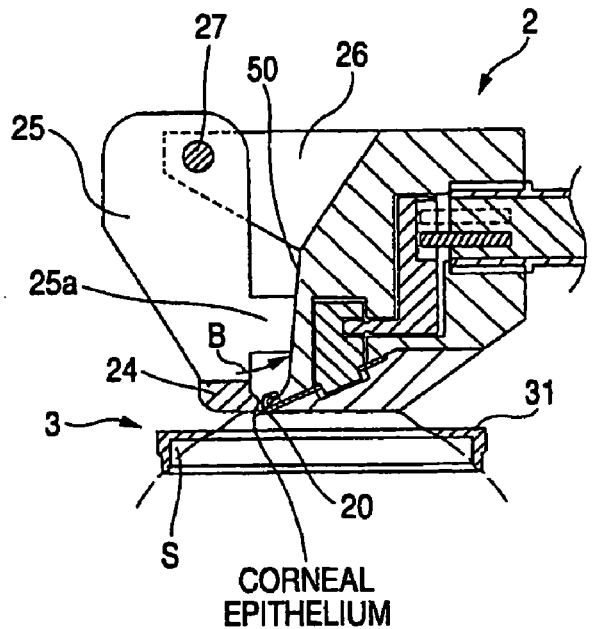
FIG. 4 presents diagrams for explaining the actions of an applanater support.
Figure 4B:
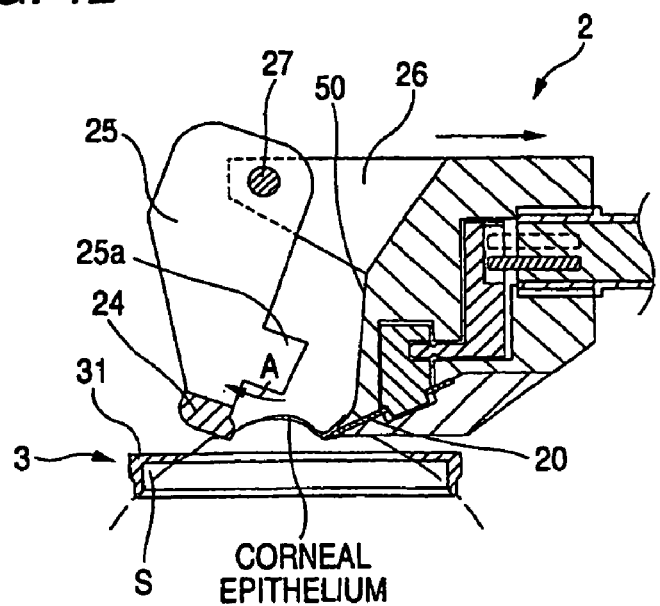

When the preparation of the corneal epithelium flap is completed (in the state of FIG. 4A), the motor 11 is reversed to move the cutting unit 2 back to the initial position. When the cutting unit 2 moves back, the forward rotating force (in the direction A) around the pin 27 is applied to the applanater 24 by the reaction from the cornea and the frictional force with the cornea, so that the applanater 24 is stopped at the position where the preparation of the corneal epithelium flap has been completed (in the state of FIG. 4B). When the cutting unit 2 is moved backward in the direction opposite to the peeling direction, the applanater support 25 supports the applanater 24 such that the distance between the applanater 24 and the cutting unit 2 (the blade 20) becomes the longer (the applanater 24 aparts from the cutting unit 2 (the blade 20)) as the cutting unit 2 moves the farther backward. As a result, no friction occurs between the corneal epithelium flap and the applanater 24 when the cutting unit 2 is returned to the initial position. Thus, it is possible to avoid the breakage of the corneal epithelium flap or the extension of the same in a direction.

When the cutting unit 2 is restored to the initial position, air is fed into the space S, and the ring 31 is removed from the patient's eye. Next, the corneal epithelium flap is opened, and the corneal stroma of a refractive correction amount is ablated by irradiating it with a laser beam. Finally, the corneal epithelium flap is returned (closed). Thus, the corneal refractive surgery is ended.

Second Embodiment

Figure 5A:
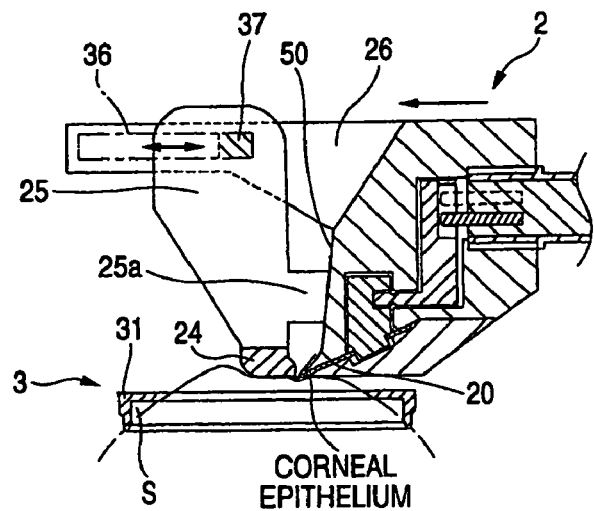
FIG. 5 presents diagrams for explaining an apparatus of a second embodiment.
Figure 5B:
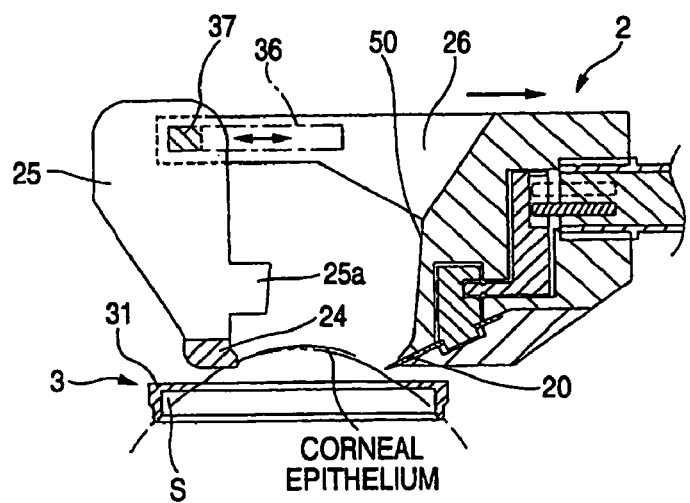

The invention has been described on the arrangement in which the applanater support 25 for supporting the applanater 24 is turned (rotated) in the peeling direction, i.e., in the forward and backward directions of the cutting unit 2 (the blade 20). However, the invention is not limited thereto. FIG. 5A and FIG. 5B are diagrams showing an apparatus according to a second embodiment. A guide recess 36 for sliding the applanater support 25 back and forth of the cutting unit 2 (the blade 20) is formed in the connecting member 26. The applanater support 25 is provided with a guide protrusion 37 for being engaged with the guide recess 36. As the cutting unit 2 moves forward in the peeling direction, the guide protrusion 37 of the applanater support 25 is positioned in the end of the guide recess 36 on the side of the body portion 1 by the reaction from the cornea and the frictional force between the cornea and the applanater 24, thereby to keep the distance constant between the applanater 24 and the cutting unit 2 (the blade 20). As a result, the cornea is applanated by the applanater 24 so that the corneal epithelium flap of a uniform thickness can be formed irrespective of the corneal shape. When the cutting unit 2 is moved backward to the initial position in the direction opposite to the peeling direction, on the other hand, the applanater 24 and the applanater support 25 are stopped at the position where the preparation of the corneal epithelium flap has been completed, by the reaction from the cornea and the frictional force between the cornea and the applanater 24. As a result, no friction between the corneal epithelium flap and the applanater 24 is generated when the cutting unit 2 is returned to the initial position, so that the corneal epithelium flap can be prevented from being broken or extended in any direction.

Third Embodiment

Figure 6A:
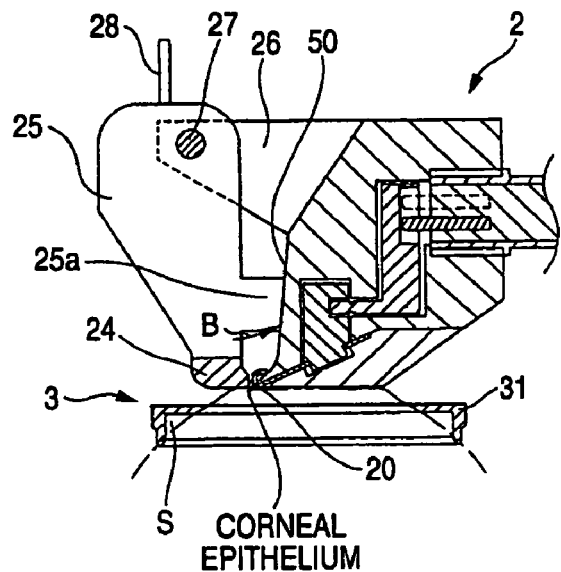
FIG. 6 presents diagrams for explaining an apparatus of a third embodiment.
Figure 6B:
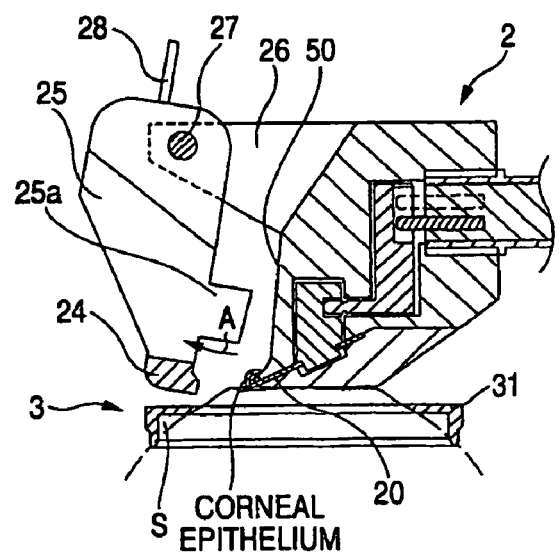

FIG. 6A and FIG. 6B are diagrams showing an apparatus according to a third embodiment. The applanater support 25 is provided at the upper portion thereof with a finger hook 28, on which the finger of an operator to grip the body portion 1 is hooked. When the finger hook 28 is hooked and pulled by the finger of the operator, the applanater support 25 is popped up forward (in the direction A) around the pin 27.

When the preparation of the corneal epithelium flap is completed (in the state of FIG. 6A), the operator hooks and pulls the finger hook 28 toward the operator. When the finger hook 28 is pulled toward the operator, the applanater support 25 is turned forward around the pin 27 so that it is popped up (to the state of FIG. 6B). With the forward turn (pop-up) of the applanater support 25, the applanater 24 is retracted from the edge of the blade 20. In other words, the distance from the cutting unit 2 (the blade 20) to the applanater 24 becomes longer (the applanater 24 aparts from the cutting unit 2 (the blade 20)) than that at the time of preparing the corneal epithelium flap.

When the cornea applanater 24 is retracted from the edge of the blade 20, air is introduced into the space to remove the ring 31 from the patient's eye. At this time, the blade 20 is extracted from the blade 20. By rotating the motor 11 backward, the cutting unit 2 is moved backward to the initial position.

With this arrangement, the cornea applanater 24 has been retracted at the time of extracting the blade 20 from the corneal epithelium flap, so that the blade 20 can be extracted without any friction with the cornea applanater 24 from the corneal epithelium flap. As a result, this corneal epithelium flap can be prevented from being broken or extended. If the apparatus is so constituted as to be extracted from the patient's eye before the cutting unit 2 is moved back to the initial position, it is possible to shorten the time period for the suction ring 31 to be sucked on the patient's eye. As a result, the operation can be performed without burdening the patient's eye.

In the foregoing arrangements, the apparatus is removed from the patient's eye before the cutting unit 2 is moved backward to the initial position. Before the apparatus is removed, however, the cutting unit 2 may be moved backward to the initial position. In this case, the cutting unit 2 may be moved backward to the initial position in a state that the cornea applanater 24 is retracted with respect to the edge of the blade 20.

Figure 7:
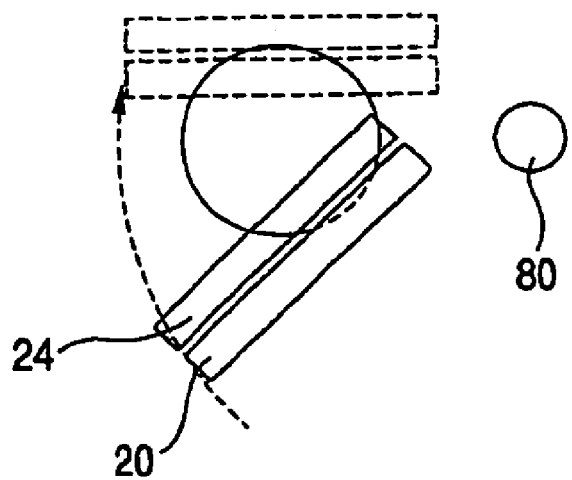
FIG. 7 is a diagram for explaining the case in which the blade is rotationally moved.

In the above-described arrangements, on the other hand, the blade is rectilinearly moved to peel the corneal epithelium. However, the invention can also be applied to the arrangement in which the blade is rotationally moved to peel the corneal epithelium. FIG. 7 is a diagram for explaining the case in which the blade is rotationally moved. When the blade 20 is moved (forward) in the peeling direction, the blade 20 is rotationally moved around a pivot pin 80 while keeping the distance constant between the cornea applanater 24 and the blade 20. After the preparation of the corneal epithelium flap is completed, the cornea applanater 24 may be retracted with respect to the edge of the blade 20. Incidentally, the detailed arrangement of the translation mechanism for moving the blade rotationally is referred to U.S. Pat. No. 5,624,456.

Fourth Embodiment

Figure 8A:
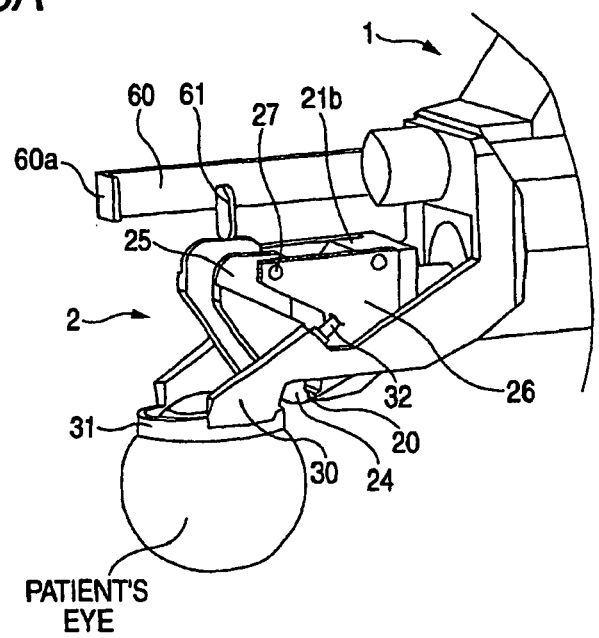
FIG. 8 presents diagrams for explaining an apparatus of a fourth embodiment.
Figure 8B:
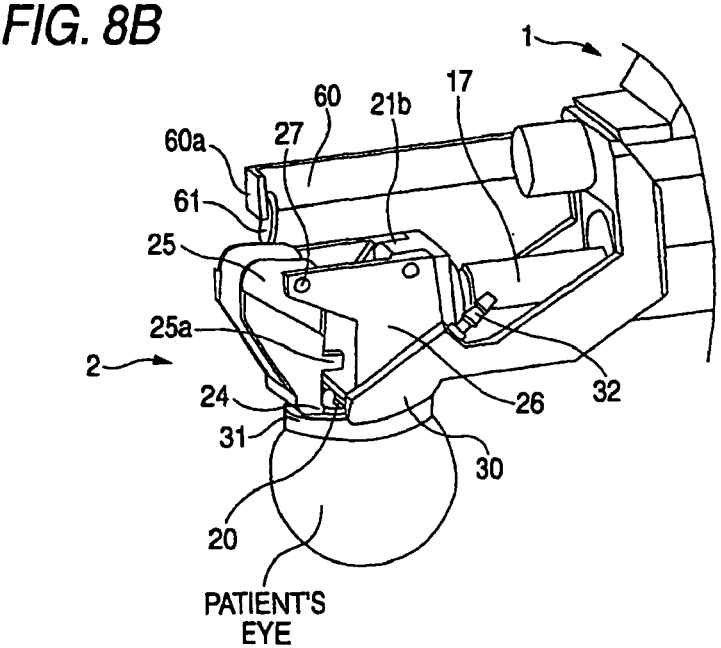

FIG. 8A and FIG. 8B are diagrams showing an apparatus according to a fourth embodiment. A retaining member 60 extending in the peeling direction is fixed to (or may be movably fixed to) the body portion 1 (or the suction ring 31). A retaining portion 60a is formed on the side of the unfixed side of the retaining member 60. An abutment portion 61 like the finger hook 28 of the third embodiment is disposed on the upper portion of the applanater support 25. When the cutting unit 2 is moved forward in the peeling direction from the initial position (in the state of FIG. 8A) to a predetermined position (where the preparation of the corneal epithelium flap is completed), the abutment portion 61 is brought to abut against the retaining portion 60a of the retaining member 60. When the cutting unit 2 is further moved forward from that predetermined position, the abutment portion 61 is retained by the retaining portion 60a and the applanater support 25 is turned and popped up in the peeling direction around the pin 27 (in the state of FIG. 8B). With this forward turn (pop-up) of the applanater support 25, the cornea applanater 24 is retracted from the edge of the blade 20. As a result, the blade 20 can be easily pulled out from the corneal epithelium flap.

Fifth Embodiment

Figure 9A:
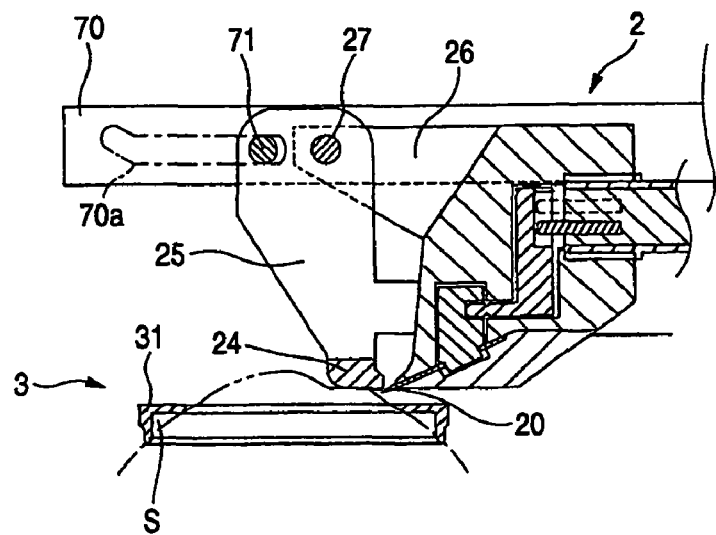
FIG. 9 presents diagrams for explaining an apparatus of a fifth embodiment.
Figure 9B:
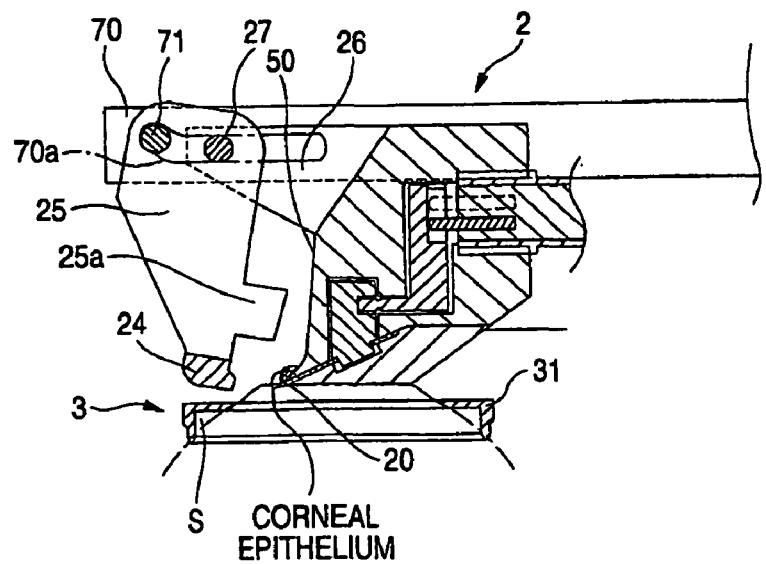

FIG. 9A and FIG. 9B are diagrams showing an apparatus according to a fifth embodiment. A stationary member 70 which has a guide recess 70a extending in the peeling direction is fixed to the body portion 1 (or the suction ring 31). On the other hand, the applanater support 25 is provided, on the front side of the pin 27, with a guide protrusion 71 to engage with the guide recess 70a. During the cutting unit 2 is moved forward in the peeling direction from the initial position and the guide protrusion 71 is in the horizontal area of the guide recess 70a (in the state of FIG. 9A), the cornea applanater 24 applanates the cornea. When the cutting unit 2 is further moved forward to a predetermined position (where the preparation of the corneal epithelium flap is completed) and the guide protrusion 71 comes to the slope area of the guide recess 70a (in the state of FIG. 9B), the applanater support 25 is turned around the pin 27 in the peeling direction to a popped-up state. With this forward turn (or pop-up) of the applanater support 25, the cornea applanater 24 is retracted from the edge of the blade 20. As a result, the blade 20 can be easily pulled out from the corneal epithelium flap.

Incidentally, as other embodiment than the above-described embodiment, the position of the cornea applanater may be changed with respect to the edge of the blade by vertically moving the applanater support.

The invention has been described on the arrangements, in which the rotating force of the motor is used as the driving forces for the oscillations of the blade 20 or the rectilinear movement (translation) of the cutting unit 2 (the blade 20), but is not limited thereto. For example, the rectilinear movement of the cutting unit 2 (the blade 20) may be manual. Moreover, the rotating force of the motor may be replaced by a pneumatic force.

The invention has been described on the arrangements, in which the body portion 1 of the corneal surgical apparatus and the cutting unit 2 are connected and fixed, but the invention may be modified such that the body portion 1 and the cutting unit 2 can be detachable from each other. Specifically, the invention can also be applied to a cutting head unit to be mounted on the body portion of the corneal surgical apparatus. In short, the invention can be applied to the cutting head unit of the so-called "disposable" type.

What is claimed is:

1. A corneal surgical apparatus for incising a cornea of a patient's eye in a flap shape, comprising:
    a suction ring adapted to be fixed on the patient's eye;
    a body portion to be gripped by an operator; and
    a cutting head unit that is movable above the suction ring with respect to the body portion rectilinearly forward from an original position by a predetermined incising distance and rectilinearly backward to return to the original position and includes a blade holder holding a blade oscillationally,
    wherein the cutting head unit includes a cornea applanater for applanating the cornea substantially flatly, an applanater support supporting the cornea applanater, and a connecting portion connecting the applanater support to the blade holder so that the cornea applanater is positioned at a front side of an edge of the blade, and
    wherein the applanater support and the connecting portion include a movable portion which has a rotating axis and allows the cornea applanater to move with respect to the blade holder so as to change a clearance between the cornea applanater and the blade holder, the movable portion allowing the cornea applanater to rotate or swing in forward and backward directions of the cutting head unit,
    wherein the applanater support has a center of gravity on a front side of the rotating axis,
    wherein the cornea applanater is supported by the applanater support connected to the blade holder by the connecting portion so as to be located at a back side of the rotating axis,
    wherein at least one of the applanater support, the connecting portion, and the blade holder includes a limit portion restricting backward movement of the cornea applanater by the movable portion such that the clearance between the cornea applanater and the holder does not become smaller than a predetermined spacing clearance,
    wherein, when the cutting head unit moves forward from the original position by the predetermined incising distance, the cornea applanater is moved together with the blade holder while the cornea applanater is always kept at the predetermined spacing clearance from the blade holder by the limit portion to always applanate the cornea prior to the blade in a state that backward rotating force or backward swinging force would be applied to the cornea applanater due to a position of the center of gravity of the applanater support and a position of the cornea applanater with respect to the rotating axis, and
    wherein, when the cutting head unit has moved backward to the original position after the cutting head unit moves forward by the predetermined incising distance, the cornea applanater is separated by a forward rotating or a forward swing of the cornea applanater from the blade holder more than the predetermined spacing clearance by the movable portion without moving backward together with the blade holder.

2. The corneal surgical apparatus according to claim 1, further comprising a finger hook to be hooked by a finger of the operator gripping the body portion so that the cornea applanater is rotated forward or swung forward and is separated from the blade holder more than the predetermined spacing clearance by the movable portion without moving backward together with the blade holder when the finger hook is pulled after the cutting head unit has moved forward by the predetermined incising distance, the finger hook being provided at the applanater support.

* * * * *